United States Patent
De Groot et al.

(10) Patent No.: US 6,747,090 B2
(45) Date of Patent: Jun. 8, 2004

(54) COMPOSITIONS CAPABLE OF FORMING HYDROGELS IN THE EYE

(75) Inventors: Jacqueline Hermina De Groot, Leek (NL); Kenneth Albert Hodd, Wales (GB); Hendrik Jan Haitjema, Peize (NL)

(73) Assignee: Pharmacia Groningen BV, Groningen (NL)

( * ) Notice: Subject to any disclaimer, the term of this patent is extended or adjusted under 35 U.S.C. 154(b) by 0 days.

(21) Appl. No.: 10/196,445

(22) Filed: Jul. 16, 2002

(65) Prior Publication Data

US 2003/0100666 A1 May 29, 2003

Related U.S. Application Data

(60) Provisional application No. 60/306,711, filed on Jul. 20, 2001.

(30) Foreign Application Priority Data

Jul. 16, 2001 (SE) ................................................ 0102543

(51) Int. Cl.[7] .................................................. C08F 20/06
(52) U.S. Cl. ...................... 524/555; 524/563; 524/560; 524/501; 623/5.11; 623/6.11; 623/6.13; 526/264; 526/330; 522/34; 522/35; 522/64; 522/111; 522/112; 522/904
(58) Field of Search ................................ 524/555, 563, 524/560, 501; 623/5.11, 6.11, 6.13; 526/264, 330; 522/34, 35, 64, 111, 112, 904

(56) References Cited

U.S. PATENT DOCUMENTS 5,665,840 A 9/1997 Pohlmann et al.
6,156,345 A * 12/2000 Chudzik et al. ............ 424/484

FOREIGN PATENT DOCUMENTS

| WO | WO9302639 | 2/1993 | |
|----|-----------|--------|---|
| WO | WO 9947185 A2 * | 9/1999 | ........... A61L/27/00 |
| WO | WO0047185 | 8/2000 | |
| WO | WO0055214 | 9/2000 | |
| WO | WO0108604 | 2/2001 | |

OTHER PUBLICATIONS

Harding et al, *Carbohydrate Polymers*, 47:109–119 (2002).

Murthy et al, *Polymer Preprints*, 40:630–631 (1999).

* cited by examiner

*Primary Examiner*—Satya Sastri
(74) *Attorney, Agent, or Firm*—Dinsmore & Shohl LLP

(57) ABSTRACT

The invention related to a hydrogel forming aqueous composition of water soluble polymers having a sufficiently high coherency that it substantially not is dispersed when being injected into an aqueous environment of a body site such as the capsular bag of the eye to undergo a photoinitiated crosslinking reaction. The water soluble polymers either can be a water-soluble polymer bearing free acrylic, or other vinylic groups capable of facile free radical reaction with a polymeric water-soluble photoinitiator also present in the composition, or a water-soluble polymer bearing both free acrylic, or other vinylic groups capable of facile free radical reaction and photoinitiator, wherein both polymers are capable of being crosslinked when irradiated with light of wavelengths greater than about 305 nm to form the hydrogel.

Figure 1:
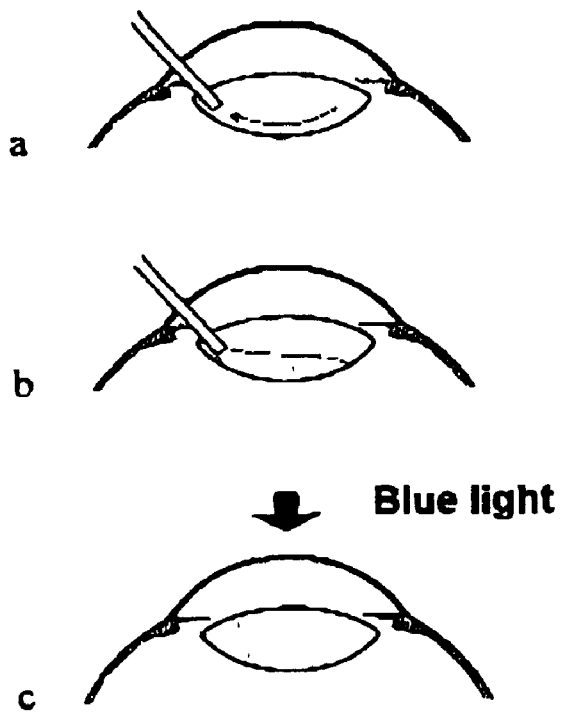

36 Claims, 1 Drawing Sheet a. extraction of the natural lens b. injection of the hydrogel solution c. irradiation with blue light a. extraction of the natural lens b. injection of the hydrogel solution c. irradiation with blue light

COMPOSITIONS CAPABLE OF FORMING HYDROGELS IN THE EYE

RELATED APPLICATION

The present application claims priority under 35 U.S.C. §119 of U.S. provisional application Serial No. 60/306,711 filed Jul. 20, 2001.

FIELD OF INVENTION

The present invention refers to aqueous solutions of reactive polymers suitable for the production of hydrogel materials upon irradiation with blue light. The hydrogels are especially useful for production-of intraocular lenses, which can be formed in-situ in the capsular bag in an eye having undergone surgical excision of a natural lens.

BACKGROUND OF THE INVENTION

The natural lens of the human eye is a precisely formed structure of fibre cells containing about 65 percent water and 35 percent organic material, chiefly structural proteins. The proteins are responsible for the relatively high refractive index of 1.42 of the lens and are structured in such a way that there are negligible local variations in their density, resulting in a transparent lens. Aging or large stresses can change the morphology of the proteins causing a progressive loss of transparency. This is termed cataract formation and is irreversible and can eventually result in blindness.

Implantation of an intraocular lens (IOL) following cataract surgery is performed to replace the optical function of the natural lens. In order to remove the natural, cataractous lens, as well as to prepare for the introduction of the IOL, an incision is made into the eye. For many years most IOLs were made of poly(methylmethacrylate), a material with good optical characteristics and compatibility with the tissues of the eye. A disadvantage of PMMA is, however, that it is a very rigid material and the incision must be made large enough, at least 5–6 mm, for implantation of the IOL. With improved devices for less traumatic removal of the natural lens by phacoemulsification, requiring only a rather small, there was a need for lenses with deformable optics. In such small incision surgery an opening of only 3 mm, or less is required. Various silicone, acrylate and hydrogel lenses have been commercialized.

All incisions in the eye are accompanied by trauma, and so, although foldable lenses have been a great improvement, there is still a need for lenses than can be placed through an even smaller incision. A lens can be implanted through a 1.2 mm opening by injecting the lens material into the capsular bag as a fluid, followed by formation of a solid full size lens in-situ in the eye. An additional advantage of this technique is that, due to the formation of a fill sized lens, complications of conventional IOL implantation namely decentration and posterior capsular opacification may be overcome. Full sized lenses show excellent centration and there is evidence that they may prevent posterior opacification (PCO). Hydrogels are a class of materials that are very interesting for an injectable lens because they have the added advantage is that their aqueous composition approximates to that of the natural lens.

Hydrogels can be made by crosslinking aqueous polymer or monomer/crosslinker solutions. Since monomers are often toxic, the use of polymers is preferred for applications in the eye. Polymers to which a reactive group is attached, for example, an acrylate group, can be polymerized in the presence of water and form a hydrogel. This is a process of crosslinking polymer or prepolymer solutions have been described before. In U.S. Pat. No. 5,665,840 crosslinkable water-soluble prepolymers based on copolymers of vinylalcohol and vinyllactams are claimed for contact lens application. Several other publications also disclose the production of hydrogels after crosslinking crosslinkable water-soluble (pre)polymers. The crosslinkable water-soluble (pre) polymers are designed to polymerize in a mould yield hydrogel. However, in-situ in the eye, water is present which demands certain specific requirements of the crosslinkable water-soluble prepolymers not described in any of these publications.

It is evident that the coherence of the aqueous solution during injection and prior to crosslinking is very important. This coherence prevents, or limits, the water in the eye from interfering with the solution before crosslinking. Without it, the carefully regulated hydrogel composition, required for generating an IOL of precise refractive index, may be diluted or altered and it is also needed to prevent leakage of polymer from the capsular bag before the polymer is crosslinked.

In addition, all hydrogels have an equilibrium water content, which is controlled both by the structure of the hydrogel and its crosslink density. Water-soluble polymers, when crosslinked, have a tendency to swell in water. For this invention it is important that after injecting the aqueous hydrogel solution into the eye, and crosslinking it, the amount of water that it takes up afterwards, the additional swelling, is limited, that is to say that the solution concentration of water in the injected hydrogel solution is equal to, or very close to, the equilibrium water concentration of the crosslinked hydrogel formed in the eye. Any additional swelling will decrease the refractive index of the lens and in more severe cases will cause collapsing of the capsular bag or even damage the eye.

A few publications and patents describe the design of injectable and crosslinkable water-soluble (pre)polymers and some polymerizations, which form hydrogels in-situ in the eye.

Ravi et al. reported in Polymer Preprints, 1999, 40, 630 on an injectable hydrogel material made by thermally curing poly(ethylenglycol) monoacrylates and diacrylates (PEGMA and PEGDA, respectively). They, were, however, not studied for possible lens refilling material but as potential probes to study the accommodation mechanism. The polymer content and, therefore, the refractive indices of the materials were very low (<1.36) and the materials showed severe swelling after curing.

In the International Patent Application WO 93/02639 an injectable collagen-based intraocular hydrogel lens is described. The concentration collagen was very low which resulted in a low refractive index of the intraocular lens (1.363). It was claimed that high refractive lenses could also be made. To achieve re-active indices closer to that of the natural lens much higher collagen concentrations are needed, than those reported in the patent, and this will increase the problem of swelling, post-injection.

In the International Patent Application WO 01/08604 it was claimed that with aqueous solutions of modified linear polymers, accommodative lenses could be prepared in-situ. The water-soluble polymers were modified to low degrees, to obtain lightly crosslinked hydrogels in order to keep the elasticity modulus of the hydrogel lenses low. The moduli of the hydrogels were measured directly after crosslinking the aqueous polymer solution. The hydrogel were, however, after crosslinking not subjected to an aqueous environment. If these materials would be made in the eye in the presence of an excess natural aqueous fluid, densities they may be expected to swell significantly due to their low crosslink density. Such swelling is to the detriment of the refractive indices of the lenses they form.

In the International Patent Application WO 00/47185, a method of producing an injectable hydrogel intraocular lens is described. The hydrogel lens materials are based on macromolecular particles. However, !the problems of obatining a suffcient coherence and avoiding additional swelling are not addressed in this disclosure.

It can be concluded that the specific requirements regarding coherence and prevention of additional swelling for injectable hydrogel lenses still needs attention if a clinically acceptable surgical process is to be attained.

DESCRIPTION OF THE INVENTION.

An object of the present invention is to provide an aqueous composition of a water soluble linear polymer that can fill the capsular bag of the eye and upon a crosslinking reaction by means of irradiation with light in the visible range can form a hydrogel intraocular lens implant of a predetermined refractive index.

It also an object of the present invention to provide an aqueous composition of a linear water soluble which has suitable coherence to avoid leaking from the capsular bag or avoiding dispersion effects in the capsular bag, while having suitably low retention time before starting the lens forming light induced crosslinking reaction.

An another object of the invention is to sufficiently crosslink the lens so that additional swelling is prevented and in this way ensure that the implanted lens permanently retains its predetermined shape and refractive value.

It is a still further object of the invention to provide hydrogel lens with no or minimal extractable polymer material.

In its most general terms the present invention pertains to an aqueous composition of a of water soluble polymers having a sufficiently high coherency that it substantially not is dispersed when being injected into an aqueous environment to undergo a crosslinking reaction into a hydrogel. The water soluble polymers can either be a water-soluble polymer bearing free acrylic, or other vinylic groups capable of facile free radical reaction with a polymeric eater-soluble photoinitiator also present in the composition, or a water-soluble polymer bearing both free acrylic, or other vinylic groups capable of facile free radical reaction and photoinitiator groups. Both these polymers will be crosslinked when irradiated with light of wavelengths greater than about 305 nm induces the photoinitiator groups to form free radicals so as to form the hydrogel. Preferably, the aqueous composition shall form a clear hydrogel with a refractive index of between about 1.36 to about 145, a transmission of visible light of at least about 35% with no, or substantially no, absorption of water from an aqueous environment during its formation or subsequently thereafter, so it becomes dimensionally stable and substantially free from swelling after the forming crosslinking process. These features will render the aqueous compositions improved properties to form an intraocular lens, in-situ in the capsular bag of the eye, from which defect natural lens has been surgically excised.

It is an important aspect of the invention that the aqueous composition has a suitable coherence to enable a surgical procedure comprising injection into the capsular bag of the eye and crosslinking to form a lens implant replacing an excised natural crystalline lens. The coherence at zero shear stress of the aqueous composition shall be sufficiently high, so that the injected composition does not leak from the capsular bag and that the composition does not disperse when injected through a standard injection needle into an aqueous environment, such as the capsular bag of the eye. It is therefore preferred that the composition has a zero shear stress viscosity of at least 3.0 Pas, preferably 10.0 Pas, and most preferably greater than 30.0 Pas. At the same time, the coherence of the inventive aqueous composition at zero shear stress must not be too high, since this will lead to an inconveniently long relaxation time of the injected aqueous composition before it is sufficiently relaxed to assume precisely the interior contours of the capsular bag and is ready to undergo crosslinking into the lens implant. An excessively coherent aqueous composition will compromise the capacity of the capsular bag to act as a forming mould for the lens surface by exerting a backpressure, with the result of an uneven or bumpy surface of the final lens implant. The coherence of an aqueous solution is determined by the interactions between the solvated polymer molecules, and the stronger these interactions the higher the coherence. These interactions derive from some combination of the generally recognized intermolecular forces, van der Waals, polar, H-bonding, and London or dispersion forces, and for polymers an additional form of interaction, chain entanglement, is a significant contributor. Chain, entanglements are physical crosslinks, which occur in polymer solutions, where the polymer has a molecular weight above a context-determined threshold. The degree of chain entanglement is also concentration dependent. These various interactions combine in any given solution to determine that solution's viscosity, and so a solution's viscosity is a useful indicator of its coherence threshold.

In order to determine if the presently invented compositions exhibit a sufficient coherency, rheological tests similar to those provided in Carbohydrate Polymers, 2000, 47, 109–119 (GS Harding et al) can be followed. According to these to tests cohesive compositions of hyaluronic acid, such as Heaton® 5, have a distinguishable behavior when flowing in PTFE, tube that are desirable for the presently invented compositions.

In the present invention the interactions between the polymer chain is determined by the chemical nature of the modified polymer the concentration and the molecular weight. Generally, a polymer modified with a hydrophobic crosslinker, will have greater coherence for a given molecular weight and concentration than a polymer modified with a hydrophilic crosslinker, where a higher molecular weight or concentration is needed for the same coherence. It is a part of the present invention to select the polymer, its molecular weight, the functional groups for crosslinking and polymer concentration in such a way that the refractive index of the aqueous solution and the coherence are in a suitable range for an injectable solution that shall form a lens implant with a controlled and predetermined refractive value.

It is a prerequisite for the present invention that the aqueous composition shall have suitable refractive to be able to provide a lens with a refractive index similar to that of the natural crystalline lens, i.e. the composition shall have a refractive index in the range of about 1.36 to 1.45. For a given hydrophilic polymer, the refractive index of a hydrogel lens is dependent upon both the mole fraction of the polymer, and the mole fraction of water in the hydrogel and the refractive index of each. Experience has shown that, for example, when polyvinyl alcohol with a refractive index of 1.51 is used to form a hydrogel, a polymer concentration of 14 to 54 wt % is needed to obtain refractive indices of 1.36 to 1–45. For the linear, water soluble, polymers employed in the present invention, the aqueous concentration required to obtain any desired refractive index will exceed the critical concentration of about 5%. Above this concentration polymer coils start to overlap and the polymer solutions to attract water, to reduce the concentration. If the equilibrium concentration is not attained during injection swelling of the formed crosslinked gel, the lens, will result as it reverts to its equilibrium water content. According to the present invention, the tendency of swelling of the finally crosslinked lens is entirely or substantially eliminated by introducing a sufficiently high crosslink density, as is dependent by the amount of the introduced functional groups for crosslinking on the linear water soluble polymers and above exemplified with acrylate groups. The interaction parameter of the polymer and the crosslinker with water will determine the optimal crosslink density. When the polymer as well as the crosslinker have a relatively high interaction parameter with water, more crosslinks are needed to prevent additional swelling, compared to a polymer and crosslinker with a lower interaction parameter. This also counts for the interaction parameter of the polymer and crosslinker separately. If the same polymer is used, and a crosslinker with a high interaction parameter is used, the needed crosslink density is higher than in case of a crosslinker with a lower interaction parameter. With the same crosslinker, a polymer with a high interaction parameter needs more crosslinks than a polymer with a low; interaction parameter. The interaction parameters $\chi$ of the polymer and cross linker will also determine the transparency of the hydrogel. When the interaction parameter of the polymer and crosslinkers are too different, this means that the two components are not miscible which will lead to phase separation and opacification of the hydrogel. For a good transmission the interaction parameters of the crosslinker and polymer should be in the same range. In a preferred embodiment hydrophilic water soluble polymers are copolymers of vinyl alcohol and have at least one monomer unit having a lactam group, such as vinyl pyrrolidone.

Further, the copolymers have at least one monomer unit capable of acting as a functional group in the crosslinking reaction, such as an acrylate group or a derivative thereof. Advantageously these monomer units are randomly distributed on the polymer chains and present in an amount yielding between about 15 and 20 mol % of acrylate groups to obtain a sufficiently high cross linking density. A complementing advantage of a highly crosslinked hydrogel according to the present invention, is that all the polymer chains are incorporated into the gel and so the system has no, or a minimum amount of extractable agents.

In one embodiment, the present; invention relates to a mixture of two water-soluble polymers of which one is a polymer having functional groups for crosslinking attached and one is a polymer having photoinitiator groups attached. The copolymers have a general formula $(A)_m(B)_n(C)_p(D)_q$ and $(A)_m(B)_n(D)_q(E)_r$ in which A can one of the following monomer, vinyl amides, vinyl lactams, acrylamide, methacrylamide, N-substitued acrylamides, N-substitued methacrylamides, vinylamine, ethyleneoxide, vinylsulfuric acids, vinylphosphonic acids, maleic acid, vinylpiperidine, vinylacrylate, methylvinylether, ethylene imine, methacrylic acid, acrylic acid, and vinylammonium salts. B is vinylalcohol or similar alcoholic group, C is a crosslinkable group attached to vinylalcohol or another alcoholic group, by its reaction with a suitable reagent such as acrylic acid chloride, methacrylic acid chloride, isocyanato acrylate, isocyanato methacrylate, epoxy acrylates, epoxy methacrylates, or itaconate or aconitate acid anhydride. D is optionally a monomer to modify the refractive index of the polymer, such as methylmethacrylate, styrene, or methyl- or benzyl-N-acetamidoacrylate, and E is a photoinitiator moiety carrying a photoinitiating group which is described per se in the International Patent Application WO 00/55214 which hereby is incorporated as a reference.

An alternative to this polymer mixture is a water-soluble copolymer to which both the functional group for crosslinking, and the photoinitiator group are attached to the and has the following general formula $(A)_m(B)_n(C)_p(D)_q(E)_r$ where A, B, C, D, E are equally as described above.

According to a preferred embodiment, the water soluble polymer has the general formula:

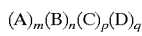

in which A, B, C and D are each are vinyl groups (—CH$_2$—CH—) to which a pyrrolidone group (A), a hydroxyl or acetate group (B), an acrylate group (C), and a photoinitiator group (D), respectively, is attached; and where the respective mole fractions of the different monomer units is: m=0.1–0.5; n=0.1 to 0.5; p=0.1–0.2; and q=0.0–0.1. The photoinitaitor groups and the acrylate groups are preferably randomly distributed on the polymer chains. Most advantageously, all groups A, B, C and D are randomly distributed along the chains in order to avoid zones with different hydrophilic characteristics which at worst may lead to phase separation and a compromised optical quality.

The photoinitiator groups are preferably selected so as to be able to bring about a crosslinking reaction induced by irradiation with blue light at a wavelength of about 400 to 500 nm. To accomplish this performance, the photoinitiator groups suitably comprise a phosphine oxide moiety. Typically suitable monomers (D) are 2,6-dimethylvinylbenzoyldiphenylphospine oxide, preferably 2,6-dimethyl-4-vinylbenzoyldiphenylphosphine oxide that typically can be present in an mole fraction of amount in the range of about 0.05 to 0.

In a specific example of the aqueous composition the water soluble polymer can follow the formula $(A)_m(B)_n(C)_p(D)_q$, wherein A, B, C and D are each are vinyl groups (—CH$_2$—CH—) to which a pyrrolido group (A), a hydroxyl or acetate group (B), an acrylate group (C), respectively is attached and where the respective mole fractions of the different monomer units are: m=0.1–0.5; n=0.1–0.5; p=0.1–0.2; and q=0. The photoinitiator is present as a separate water soluble polymer entity, which is a copolymer of 2,6-dimethyl-4-vinylbenzoyldiphenylphosphine oxide and N,N-dimethylacrylamide with 2,6-dimethyl-4-vinylbenzoyldiphenylphosphine oxide present in the water soluble photoinitiator in mole fractions in the range of 0.05 to 0.25. Alternatively, the photoinitiator is present as a separate water soluble polymer having the formula $(A)_m(B)_n(D)_q$, wherein A, B and D are each are vinyl groups (—CH$_2$—CH—) to which a pyrrolidone group (A), a hydroxyl or acetate group (B), and a photoinitiator group (D), respectively, is attached; and where the respective mole fractions of the different monomer units is: m=0.1 to 0.5; n=0.1 to 0.5 and q=0.05–0.25. In the photoinitaitor group (D) the phosphine oxide can be linked to the vinyl groups through a urethane band as outlined in detail in the above mentioned WO 00/55214. In this specific example of the invention the water soluble polymer to be reacted with the polymeric photoinitiator suitably is a copolymer of vinyl pyrrolidone and vinyl alcohol wherein a fraction of the hydroxyl groups modified with a functional acryl group for crosslinking. Typically about 15 to 20 mol % of the hydroxyls are modified in order to obtain the suitable crosslinking density as earlier discussed.

The aqueous compositions so far disclosed typically will find use in methods of forming a rigid and dimensionally stable hydrogel intraocular lens in situ in the eye by. The compositions will be injected with a conventional syringe into the capsular bag of the aphakic eye. Due to the suitable coherence and viscosity of the composition this can be performed without complications in the form high injection pressure, air bubble formation or material dispersion which otherwise may jeopardize patient safety or lens quality. Subsequent to injection and relaxation of the material the eye is irradiated with a sufficient amount of light exceeding about 305 nm, preferably with blue light to form the hydrogel lens The present invention also relates a method of forming a dimensionally stable clear hydrogel that includes at first the provision of a vinyl alcohol monomer containing polymer having a refractive index of at least 1.41. A first part of the polymer is chemically modified so a sufficient amount of a first part of said vinyl alcohol monomers obtains functional acrylic groups for crosslinking. A second part of said vinyl alcohol containing polymer is chemically modified by attaching a blue light activated photoactive group comprising a phosphine oxide moiety, for example by means of an urethane bond, so as to obtain a polymeric water soluble photoinitaitor. The first and second part is mixed into an injectable aqueous composition with a sufficient polymer concentration to obtain a refractive index of about 1.36 to 1.45. Finally, the composition is injected into the eye or into another body site and irradiated with light of a wavelength exceeding about 400 nm, so as to form a hydrogel by means of crosslinking.

Besides preparation of intraocular lenses the inventive aqueous hydrogel foxing compositions will find use in numerous other medical applications including tissue engineering, tissue adhesive processes. The hydrogels may also act as slow release or depot formulations for a wide variety of pharmaceuticals as for example illustrated by, but not limited to agents that inhibit epithelial cell growth on an implanted intraocular lens.

The following detailed description aims to illustrate examples of hydrogels according to present invention and should not be regarded as limiting for the scope of the invention or its applicability.

DETAILED AND EXEMPLIFYING PART OF THE DESCRIPTION

FIG. 1 shows a surgical procedure for the formation of an IOL in a pig's eye with a hydrogel forming composition according to the invention

EXAMPLES: 1
Modification of Water-Soluble Polymers with Reactive Groups

EXAMPLE 1A
Methanolysis of N-vinylpyrrolidone/vinylacetate (60/40) Copolymer The acetate groups of the copolymer were hydrolyzed by dissolving the copolymer (40.0 g, 0.16 mol acetate groups, Mw 60000, Mn 20000) in methanol (200 ml). A solution of NaOH (6.4 g, 0.16 loll in water (8 ml) was added to the solution. The solution was heated to 40° C. for 24 h and afterwards neutralized with 2M HCl. The solution was poured into dialyzing tubes (Spectrapor 2000 MWCO 1000) and dialyzed against frequently refreshed reversed osmosis (RO) water for two days. The polymer solution was concentrated in al rotary evaporator, diluted with methanol (100 ml) and precipitated in diethylether (1l). The polymer, copoly(N-vinylpyrrolidone/vinylalcohol) copoly(NVP/VA), was dried in an oven, pulverized and further dried in a vacuum oven connected to an oil pump above Sicapent for at least one week. The oven was ventilated with nitrogen to prevent water absorption. The degree of hydrolysis was checked with IR (Perkin Elmer Spectrum 1).

EXAMPLE 1B
Acrylation of NVP/VA Copolymer

Dried copoly(NVP/VAC) 60/40 (2.0 g, 9.5 mmol OH groups, from example 1A) was dissolved in 45 ml DMAC at 40° C. under nitrogen atmosphere. 5 ml solution of 6–9 ml acryloylchloride in 43.1 ml DMAC (8.5 mmol) was added slowly to the polymer solution at room temperature. A small amount of methylhydroquinone was added and the solution was heated to 40° C. overnight. The reaction mixture was protected from light by aluminum foil. The solution was neutralized with a small amount of sodium bicarbonate. The polymer was precipitated in diethylether and redissolved in 25 ml methanol to precipitate the salts. The solutions was decanted and precipitated in a 10-fold excess of diethylether. The polymer was dried in a vacuum stove. The degree of modification was determined by $^1$H nmr (Varian Unity 300).

EXAMPLE 1C
Introduction of Phosphineoxide Groups

This reaction was performed in subdued light under an inert nitrogen atmosphere. To an oven dried three-neck flask 18.5 mol % acrylate modified copoly(NVP/VA) (2 g, xmmol), as is described in example 18 was dissolved in 25 ml DMSO. To this solution, 4-isocyanato-3,5-dimethylbenzoyldiphenylphosphineoxide (0.2 g, ymmol) in 10 ml DMAC was added at 40° C. After standing overnight the reaction mixture was poured into an excess of diethylether. The light yellow polymer precipitated was collected by filtration, dissolved in methanol (30 ml) and reprecipitated in ether. The polymer was dried in a vacuum oven at room temperature. A $^1$H-NMR scan in DMSO-d6 of the phosphineoxide modified acrylated copoly(NVP/VA) revealed that the PO substitution was 1.1 mol %

EXAMPLE 2
The Photopolymerization of a Series of Polyethyleneglycol Diacrylates PEGDA. (MWs in the Range 250 to 4000D)

EXAMPLE 2A

A polymeric acylphosphineoxide photocrosslinker (0.050 g), for which the synthesis is described in WO 00/55214, and PEGDA (0.450 g) of which the molecular weight of the PEG part was 258, were dissolved in 0.5 g saline under dark circumstances. The solution was sucked into a syringe with an 18 G needle. The solution was poured between two microscopic glass plates separated by teflon spacer (diameter 1 cm, thickness of 4 mm). The mould was illuminated with blue light (500 mW/cm$^2$) for 2 minutes. The appearance, equilibrium water content, mass loss and transmission are presented in table 1.

EXAMPLES 2B TO 2O

The appearance, equilibrium water content, extractables and transmission of other gels prepared, in like manner to example 2A, from PEGDAs in a range of PEG MWs from 258 to 4000D are also collected in table 1.

EXAMPLE 3
Photopolymerization of Acrylate Modified Copoly(NVP/VA)

EXAMPLE 3A 0.025 g PPI and 0.475 g, 2.0 mol %-acrylate modified copoly(NVP/VA), were dissolved in 0.5 g saline in the dark. The solution was sucked into a syringe with an 18 G needle. The polymer solution in the syringe was degassed by centrifugation at 3000 rpm. The solution was injected into a casting cell to produce a sample of a photocast gel as described in example 2A. The appearance, equilibrium water content, mass loss and transmission of this gel (3A) are presented in table 2.

EXAMPLES 3B TO 3S

The appearance, equilibrium water content, mass loss and transmission of Examples 3B to 3S, which are of gels were prepared in like manner to Example 3A, are also collected in Table 2.

EXAMPLE 4

Method described in example 3A was repeated with 0.5 g polymer described in example 1B. The hydrogel was comparable to hydrogel described in example 3L.

EXAMPLE 5

The in-vitro Photopolymerization of Hydrogels in the Capsular Bags of Pigs' Eyes

EXAMPLE 5A

The surgical procedure of the lens formation in the capsular bag of an extracted pig's eye is shown in FIG. 1. After removal of the natural lens, a solution of photocurable hydrogel with a viscosity at zero shear rate of 0.15 Pas, as is described in example 3L, was injected into the capsular bag and cured by irradiating with blue light at 2 W/cm$^2$.

EXAMPLES 5B TO 5G

Following the method described for example SA lenses were prepared in pigs' eyes from hydrogel solutions with

TABLE 1

Photocuring of polyethyleneglycoldiacrylates (PEGDA) with a polymeric phosphine oxide photoinitiator (PPI)

| Example | PPI (wt % of PEGDA) | PEGDA + PPI (wt % in H$_2$O) | PEGDA (MW D) | Curing Times (at 0.5 Wcm$^2$) | Appearance Of Gel | EWC$^a$ (wt %) | Extractables (wt %) | Transmission (% @ 480 nm) |
|---|---|---|---|---|---|---|---|---|
| 2A | 10.0 | 50 | 258 | 120 | White | 70 ± 1 | —$^b$ | — |
| 2B | 10.0 | 50 | 575 | 120 | Opaque | 55 ± 1 | — | — |
| 2C | 10.0 | 50 | 700 | 120 | Slightly opaque | 56 ± 1 | — | — |
| 2D | 10.0 | 50 | 4000 | 120 | Clear | 89 ± 1 | — | — |
| 2E | 1.0 | 50 | 700 | 120 | Clear | 54 ± 1 | — | — |
| 2F | 2.5 | 50 | 700 | 120 | Clear | 54 ± 1 | — | — |
| 2G | 5.0 | 50 | 700 | 120 | Clear | 54 ± 1 | — | — |
| 2H | 5.0 | 50 | 700 | 10 s | Clear | 54 ± 1 | 1.7 ± 0.5 | 89 ± 1 |
| 2I | 5.0 | 50 | 700 | 30 s | Clear | 54 ± 1 | 1.4 ± 0.5 | 91 ± 1 |
| 2J | 5.0 | 50 | 700 | 120 s | Clear | 54 ± 1 | 0.9 ± 0.5 | 84 ± 1 |
| 2K | 5.0 | 50 | 700 | 150 s | Clear | 54 ± 1 | 1.4 ± 0.5 | 87 ± 1 |
| 2L | 0.5 | 50 | 700 | 30 s (at 2.0 Wcm$^2$) | Clear | 57 ± 1 | 1.5 ± 0.5 | 76 ± 1 |
| 2M | 1.0 | 50 | 700 | 30 s (at 2.0 Wcm$^2$) | Clear | 54 ± 1 | 0.7 ± 0.5 | 90 ± 1 |
| 2N | 2.5 | 50 | 700 | 30 s (at 2.0 Wcm$^2$) | Clear | 54 ± 1 | 1.2 ± 0.5 | 90 ± 1 |
| 2O | 5.0 | 50 | 700 | 30 s (at 2.0 Wcm$^2$) | Clear | 54 ± 1 | 1.0 ± 0.5 | 91 ± 1 |

$^a$Equilibrium water content, $^b$not measured

TABLE 2

Cast gels prepared by photopolymerisation of acrylated copolyNVP/VA & PPI

| Example # | PPI (wt % of NVP/VA) | PPI + NVP/VA (wt % in H$_2$O) | Acrylate (mole % of NVP/VA) | Curing time (min @ 0.5 W) | Appearance | EWC$^a$ (wt %) | MassLoss (wt %) | Transmission (% @ 480 nm) |
|---|---|---|---|---|---|---|---|---|
| 3A | 5.0 | 50 | 2.0 ± 0.5 | 2 | White | 81 ± 1 | —$^b$ | — |
| 3B | 5.0 | 50 | 4.5 ± 0.5 | 2 | Opaque | 78 ± 1 | — | — |
| 3C | 5.0 | 50 | 8.0 ± 0.5 | 2 | Opaque | 56 ± 1 | — | — |
| 3D | 5.0 | 50 | 12.0 ± 0.5 | 2 | Slightly opaque | 52 ± 1 | — | — |
| 3E | 5.0 | 50 | 15.0 ± 0.5 | 2 | Translucent | 52 ± 1 | — | — |
| 3F | 5.0 | 50 | 16.2 ± 0.5 | 2 | Yellow clear | 52 ± 1 | 0.0 | 25 ± 1 |
| 3G | 5.0 | 50 | 17.7 ± 0.5 | 2 | Yellow clear | 52 ± 1 | 0.0 | 28 ± 1 |
| 3H | 5.0 | 50 | 19.9 ± 0.5 | 2 | Translucent | 52 ± 1 | — | — |
| 3I | 5.0 | 50 | 18.5 ± 0.5 | 0.5 | Fluid | — | — | — |
| 3J | 5.0 | 50 | 18.5 ± 0.5 | 1 | Fluid | — | — | — |
| 3K | 5.0 | 50 | 18.5 ± 0.5 | 1.5 | White pieces | — | — | — |
| 3L | 5.0 | 50 | 18.5 ± 0.5 | 2 | Yellow clear | 52 ± 1 | 0.0 ± 0.5 | 33 ± 1 |
| 3M | 5.0 | 50 | 18.5 ± 0.5 | 3 | Yellow clear | 52 ± 1 | 0.0 ± 0.5 | 35 ± 1 |
| 3N | 5.0 | 50 | 18.5 ± 0.5 | 4 | Yellow clear | 51 ± 1 | 0.0 ± 0.5 | 37 ± 1 |
| 3O | 5.0 | 50 | 18.5 ± 0.5 | 2(@ 2 Wcm$^2$) | Yellow clear | 51 ± 1 | 0.0 ± 0.5 | 40 ± 1 |
| 3P | 1.0 | 50 | 15.0 ± 0.5 | 2 | Fluid | — | — | — |
| 3Q | 2.5 | 50 | 15.0 ± 0.5 | 2 | Opaque | — | — | — |
| 3R | 5.0 | 50 | 15.0 ± 0.5 | 2 | Yellow clear | — | — | — |
| 3S | 10 | 50 | 15.0 ± 0.5 | 2 | Opaque | — | — | — |

$^a$Equilibrium water content, $^b$not measured viscosities at zero shear rate in the range 0.80 to 200 Pas. The shapes of the lenses formed are presented in Table 3.

TABLE 3

Viscosities at zero shear rate of solutions used to form lenses in pigs' eyes and the resulting lens shapes.

| Example # | η (Pas) | Lens shape[a] |
|---|---|---|
| 5A | 0.15 | − |
| 5B | 0.80 | − |
| 5C | 3.0 | ± |
| 5D | 12 | + |
| 5E | 30 | + |
| 5F | 80 | + |
| 5G | 200 | + |

[a]Incompletely formed "−"
Partially formed "±"
Well formed "+"

What is claimed is:

1. An aqueous composition of water soluble polymer, the composition having a coherency effective to substantially prevent dispersion when the composition is injected into an aqueous environment to undergo a crosslinking reaction into a hydrogel and having a zero shear stress viscosity of at least 10.0 Pas, wherein the water soluble polymer comprises (i) a water-soluble polymer bearing free acrylic or other vinylic groups capable of facile free radical reaction with a polymeric water-soluble photoinitiator present in the composition, or (ii) a water-soluble polymer bearing both free acrylic or other vinylic groups capable of facile free radical reaction and photoinitiator groups, wherein the water-soluble polymer is a linear polymer capable of providing the hydrogel with (i) a refractive index of between about 1.36 and about 1.45; (ii) a transmission of visible light of at least about 35%; and (iii) no or substantially no absorption of water from an aqueous environment during hydrogel formation or subsequently, whereby the hydrogel is dimensionally stable and substantially free from swelling, and wherein the water-soluble polymer is capable of being crosslinked when irradiated with light of wavelength greater than about 305 nm to form the hydrogel.

2. An aqueous composition according to claim 1, wherein said water soluble polymer is a copolymer of vinyl alcohol.

3. A composition according to claim 2, wherein said copolymer has at least one monomer unit having a lactam group.

4. A composition according to claim 2, wherein said monomer unit is vinyl pyrrolidone.

5. A composition according to claim 2, wherein said copolymer has at least one monomer unit capable of acting as a functional group in the crosslinking reaction.

6. A composition according to claim 5, wherein said monomer unit comprises an acrylate group or a derivative thereof.

7. A composition according to claim 6, wherein said monomer unit is randomly distributed on the polymer chains.

8. A composition according to claim 6, wherein said polymer comprises between about 15 and 20 mol % of said acrylate groups.

9. A composition according to claim 1 wherein the water soluble polymer has the general formula $(A)_m(B)_n(C)_p(D)_q$ 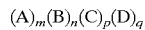 or $(A)_m(B)_n(D)_q(E)_r$ in which A is selected from the group consisting of the following monomers: vinyl amides, vinyl lactams, acrylamide, methacrylamide, N-substituted acrylamides, N-substituted methacrylamides, vinylamine, ethyleneoxide, vinylsulfuric acids, vinylphosphonic acids, maleic acid, vinylpiperidine, vinylacrylate, methylvinylether, ethylene imine, methacrylic acid, acrylic acid, and vinylammonium salts; B is vinylalcohol or another alcoholic group; C is a crosslinkable group attached to vinylalcohol or another alcoholic group, by reaction with a reagent comprising acrylic acid chloride, methacrylic acid chloride, isocyanato acrylate, isocyanato methacrylate, epoxy acrylates, epoxy methacrylates, itaconate acid anhydride or aconitate acid anhydride; D is optional and is a monomer to modify the refractive index of the polymer; and E is a photoinitiator moiety carrying a photoinitiating group, and wherein the respective mol fractions of the monomer units are m=0.1 to 0.5, n=0.1 to 0.5, p=0.1 to 0.2, q=0.0 to 0.1 and r=0.05 to 0.25.

10. A composition according to claim 2, wherein said water soluble polymer has the general formula:

$$(A)_m(B)_n(C)_p(D)_q$$

in which A, B, C and D are each vinyl groups (—CH$_2$—CH—) to which a pyrrolidone group (A), a hydroxyl or acetate group (B), an acrylate group (C), and a photoinitiator group (D), respectively, is attached; and where the respective mole fractions of the monomer units is: m=0.1 to 0.5; n=0.1 to 0.5; p=0.1 to 0.2; and q=0.0 to 0.1.

11. A composition according to claim 10, wherein said photoinitiator group is randomly distributed on the polymer chains.

12. A composition according to claim 1, wherein the crosslinking reaction is performed with blue light at a wavelength of about 400 to 500 nm.

13. A composition according to claim 11, wherein the photoinitiator group comprises a phosphine oxide moiety.

14. A composition according to claim 13, wherein the monomer unit bearing the phosphine oxide moiety is 2,6-dimethylvinylbenzoyldiphenylphosphine oxide.

15. A composition according to claim 1, comprising a water soluble polymer comprising a copolymer of vinyl alcohol and free of monomers bearing photoinitiator groups, and a water soluble polymeric photoinitiator bearing photoinitiator groups comprising a copolymer of 2,6-dimethyl-4-vinylbenzoyldiphenylphosphine oxide and N,N-dimethylacrylamide.

16. A composition according to claim 15, wherein the 2,6-dimethyl-4-vinylbenzoyldiphenylphosphine oxide is present in the water soluble photoinitiator in a mole fraction in the range of 0.05 to 0.25.

17. A composition according to claim 1 comprising a water soluble polymer comprising a copolymer of vinyl alcohol and free of monomers bearing photoinitiator groups, and a water soluble polymeric photoinitiator having the formula:

$$(A)_m(B)_n(D)_q$$

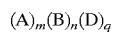

in which A, B and D are each are vinyl groups (—CH$_2$—CH—) to which a pyrrolidone group (A), a hydroxyl or acetate group (B), and a photoinitiator group (D), respectively, is attached; and where the respective mole fractions of the monomer units is: m=0.1 to 0.5; n=0.1 to 0.5; and q=0.05 to 0.25.

18. An aqueous composition of water soluble polymer and a polymeric water-soluble photoinitiator, the composition having a coherency effective to substantially prevent dispersion when the composition is injected into an aqueous environment to undergo a crosslinking reaction into a hydrogel, wherein the water soluble polymer is free of photoinitiator groups, has free acrylic or other vinylic groups capable of facile free radical reaction with the polymeric water-soluble photoinitiator, and is capable of being crosslinked when irradiated with light of wavelengths greater than about 305 nm to form the hydro gel, wherein the water soluble polymeric photoinitiator has the formula:

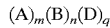

in which A, B and D are each are vinyl groups (—CH$_2$—CH—) to which a pyrrolidone group (A), a hydroxyl or acetate group (B), and a photoinitiator group (D), respectively, is attached; and where the respective mole fractions of the monomer units is: m=0.1 to 0.5; n=0.1 to 0.5; and q=0.05 to 0.25, and wherein the photoinitiator group comprises a phosphine oxide moiety linked to the main polymer chain by a urethane bond.

19. An aqueous composition of water soluble polymer and a polymeric water-soluble photoinitiator, the composition having a coherency effective to substantially prevent dispersion when the composition is injected into an aqueous environment to undergo a crosslinking reaction into a hydrogel, wherein the water soluble polymer is free of photoinitiator groups, has free acrylic or other vinylic groups capable of facile free radical reaction with the polymeric water-soluble photoinitiator, is a copolymer of vinylpyrrolidone and vinyl alcohol having a fraction of its hydroxyl groups modified with a functional acryl group for crosslinking, and is capable of being crosslinked when irradiated with light of wavelengths greater than about 305 nm to form the hydrogel, and wherein the water soluble polymeric photoinitiator has the formula:

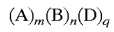

in which A, B and D are each are vinyl groups (—CH$_2$—CH—) to which a pyrrolidone group (A), a hydroxyl or acetate group (B), and a photoinitiator group (D), respectively, is attached; and where the respective mole fractions of the monomer units is: m=0.1 to 0.5; n=0.1 to 0.5; and q=0.05 to 0.25.

20. A composition according to claim 19, wherein the water soluble polymeric photoinitiator is a copolymer of vinylpyrrolidone and vinyl alcohol having phosphine oxide moieties attached thereto by means of a urethane bond.

21. A composition according to claim 1, wherein the concentration of polymer is about 14 to 54 wt %.

22. A method of forming a rigid and dimensionally stable hydrogel intraocular lens in situ in the eye, comprising injecting a composition according to claim 1 into the capsular bag of an aphakic eye, and irradiating said eye with a sufficient amount of light exceeding about 305 nm, thereby forming the hydrogel lens.

23. An intraocular lens formed from the composition according claim 1.

24. A method of forming a dimensionally stable, clear hydrogel, comprising the steps of (i) providing a vinyl alcohol monomer-containing polymer having a refractive index of at least 1.41;

(ii) chemically modifying a sufficient amount of a first part of vinyl alcohol monomers in said vinyl alcohol monomer-containing polymer so as to obtain a hydrophilic water soluble polymer having functional acrylic groups for crosslinking;

(iii) chemically modifying a second part of said vinyl alcohol monomer-containing polymer by attaching a blue light activated photoactive group comprising a phosphine oxide moiety by means of an urethane bond to obtain a polymeric water soluble photoinitiator;

(iv) providing an injectable aqueous composition of said first and second parts, said composition having a refractive index of about 1.36 to 1.45; and (v) irradiating said aqueous composition with light of a wavelength exceeding about 400 nm, to form a hydrogel by means of crosslinking.

25. A method according to claim 24, wherein the vinyl alcohol monomers of step (ii) are modified with an acrylic acid chloride.

26. A method according to claim 24, wherein about 15 to 20 mol % of acrylate groups are introduced.

27. A method according to claim 24, wherein the vinyl alcohol monomer-containing polymer is a copolymer of polyvinyl pyrrolidone and vinyl alcohol.

28. A method according to claim 24, wherein the aqueous composition provided in step (iv) has a zero shear stress viscosity of at least 3.0 Pas.

29. A hydrogel formed by the method of claim 24, having a water equilibrium content less than about 50% wt and a transmission of light at 480 nm in the range of 35 to 45%, and being substantially free from additional swelling after crosslinking.

30. An aqueous composition according to claim 1, having a zero shear stress viscosity greater than 30.0 Pas.

31. A composition according to claim 9, wherein D is methyl methacrylate, styrene, methyl-N-acetamidoacrylate, or benzyl-N-acetamidoacrylate.

32. A composition according to claim 13, wherein the monomer unit bearing the phosphine oxide moiety is 2,6-dimethyl-4-vinylbenzoyldiphenylphosphine oxide.

33. An aqueous composition according to claim 1, wherein the water-soluble polymer bears about 15 to 20 mol % of acrylate groups.

34. A method according to claim 24, wherein the water-soluble polymer bears about 15 to 20 mol % of acrylate groups.

35. A method according to claim 24, wherein the aqueous composition provided in step (iv) has a zero shear stress viscosity of at least 10.0 Pas.

36. A method according to claim 24, wherein the aqueous composition provided in step (iv) has a zero shear stress viscosity greater than 30.0 Pas.

* * * * *

UNITED STATES PATENT AND TRADEMARK OFFICE
CERTIFICATE OF CORRECTION

PATENT NO.    : 6,747,090 B2
DATED         : June 8, 2004
INVENTOR(S)   : Jacqueline H. DeGroot et al.

It is certified that error appears in the above-identified patent and that said Letters Patent is hereby corrected as shown below:

Column 11,
Line 52, change "claim 2" to -- claim 3 --

Signed and Sealed this

Tenth Day of August, 2004

JON W. DUDAS
*Acting Director of the United States Patent and Trademark Office*